(12) United States Patent
Ragsdale et al.

(10) Patent No.: US 6,258,592 B1
(45) Date of Patent: Jul. 10, 2001

(54) ELECTROPORATION CELL WITH ARC PREVENTION/REDUCTION

(75) Inventors: Charles W. Ragsdale, Concord; John Tagliamonte, Albany, both of CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/410,966

(22) Filed: Oct. 5, 1999

Related U.S. Application Data (60) Provisional application No. 60/139,019, filed on Jun. 14, 1999.

(51) Int. Cl.$^7$ ..................................................... C12M 1/42
(52) U.S. Cl. ........................... 435/285.2; 435/461; 218/4; 361/6
(58) Field of Search ................................. 435/285.2, 461; 218/4; 361/6

(56) References Cited

U.S. PATENT DOCUMENTS

| | | | |
|---|---|---|---|
| 4,923,814 | * 5/1990 | Marshall | 435/173 |
| 5,656,926 | * 8/1997 | Ragsdale | 323/282 |

* cited by examiner

*Primary Examiner*—James Ketter
(74) *Attorney, Agent, or Firm*—Townsend & Townsend & Crew LLP; William E. Winters (57) ABSTRACT

An electroporation system and method for directing high-voltage currents to a suspension of cells contained in a cuvette. A high-voltage switch controls the coupling of a charge control to a high-voltage capacitor and, additionally, controls the coupling of the high-voltage capacitor to the cuvette. A current diverter diverts current away from the sample whenever an arc condition commences or a low sample resistance is detected across the cuvette. The current diverter includes a current diverter switch, which is triggered when a sense resistor measures a second predetermined voltage indicative of an arc-over event (or a low sample resistance condition).

19 Claims, 7 Drawing Sheets

ELECTROPORATION CELL WITH ARC PREVENTION/REDUCTION

This application claims benefit of Provisional Application Ser. No. 60/139,019 filed Jun. 14, 1999.

BACKGROUND OF THE INVENTION

The present invention relates generally to cell transfection, and, more particularly, to an apparatus and method of electroporation that prevents and/or reduces arcing across a cuvette containing a sample of biological cells.

Electroporation is a process by which high-voltage (typically high energy) electric potentials are used to create temporary holes ("pores") in the walls of biological cells. These pores allow the passage of large molecules (e.g., DNA) into the cell, before the cell eventually closes the pores. As a consequence, electroporation can be used to program a cell to produce proteins specified by the DNA (bacterial cells for example can be caused to produce human insulin). Electroporation is, therefore, an extremely powerful tool, since a 5-msec application of a high-energy pulse can create openings in millions of cells at the same time. Cells that have received DNA in this manner can then be grown in a nutritive broth to produce an aggregate, which generates large quantities of some desirable complex molecule. Typically, a biological cell can produce compounds in seconds or minutes whereas a conventional synthesis may require a week or more when performed in a laboratory using chemical synthesis procedures.

Previous patents (U.S. Pat. Nos. 4,750,100, 5,656,926 and 5,642,035), each of which is incorporated herein by reference, describe the use of semiconductor-controlled rectifiers (SCRs) in a stacked-cell arrangement to produce a solid-state high-voltage (HV) switch capable of controlling 3000V pulses at currents of 1500 amperes (or higher, depending on the SCR). Increasing the number of SCR cells allows the control of higher voltage pulses. The general method of producing such pulses is shown in FIG. 1 attached hereto.

Figure 1:
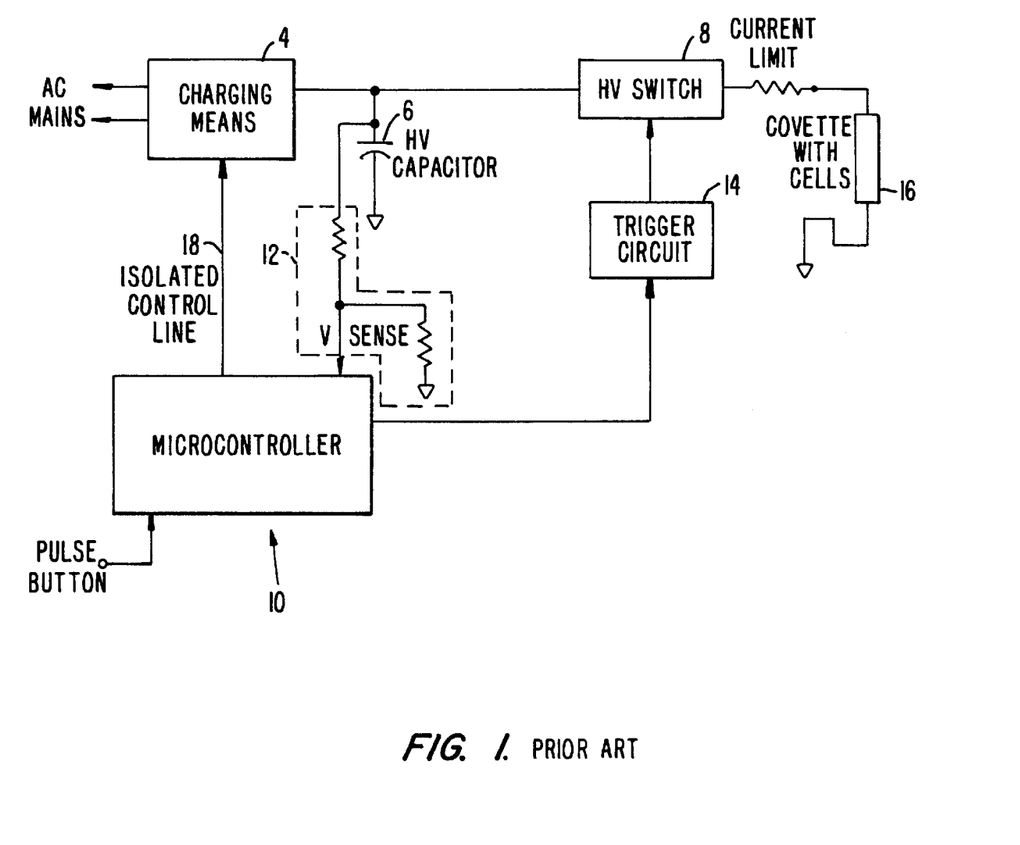
FIG. 1 is a block diagram of a solid-state HV switch lacking the arc prevention/reduction features of the present invention.

In FIG. 1, a charging means 4, consisting of a linear or switcher current source, is controlled by a microcontroller 10 through an isolated control line 18. The microcontroller 10 turns on the charging means 4, thereby causing charge to accumulate in an HV capacitor 6. As the voltage across the HV capacitor 6 rises, the microcontroller 10 monitors the increasing voltage, using a voltage divider 12 consisting of two or more resistors. When the voltage has reached a predetermined value, either by embedded program or external setting by an operator, the microcontroller 10 triggers the HV switch 8 (consisting of the SCR cells) through a trigger circuit 14. The HV switch 8 effectively connects the HV capacitor 6 to the output of the system, which in turn connects to a cuvette 16 or other sample holder containing cells and DNA (or other) compounds. The resistance of the sample in the cuvette 16 may be effectively 10 ohms at high voltage. Hence, without a current limiting resistor, large currents could flow and destroy the HV switch 8. Later embodiments, such as those in U.S. Pat. Nos. 5,656,926 and 5,642,035, for example, use a 1.5-ohm series resistor with feedback through the microcontroller to compensate for voltage drops across the resistor.

Another concern in the use of such a system is arc-over. If the voltage at the cuvette 16 is too high, an arc-over may occur. Arc-overs lower the cuvette's 16 effective resistance to 1.0 ohms or less. Hence, at 3000V (with 1.5 ohms current limiting resistance), 2000 amperes may flow. Typical SCRs used for such an application will tolerate such currents. However, the arc will cause a visible and auditory event at the cuvette 16, which may expel the sample, destroy cells, and startle the operator.

In the electroporator system of U.S. Pat. No. 4,750,100, no specific current limiting resistor is incorporated, since such a resistor would cause a large voltage drop. (The resistance required by the resistor would have to be 1.5 ohms, which is significant compared to that of the sample, whose resistance is 10 ohms.) U.S. Pat. No. 4,750,100 does, however, describe the use of the SCR cells to produce an appropriate HV switch. In U.S. Pat. Nos. 5,656,926 and 5,642,035 a system that measures sample resistance is included. This allows the microprocessor to compensate for the voltage drop across a current limiting resistor by charging the HV capacitor to a somewhat higher voltage. Other novel portions of the design are described in the same two patents.

Lack of arc protection in the electroporator system of U.S. Pat. No. 4,750,100 was acceptable since arcs were infrequent, until the system was later used on bacterial cells. Bacteria require the use of higher voltages, thereby increasing the likelihood of arcs. Bacteria electroporation in those systems requires a special box containing the current limiting resistor (which might be forgotten by the user to the detriment of the instrument) or the incorporated arc protection of the instruments disclosed in U.S. Pat. Nos. 5,656,926 and 5,642,035.

A better system would be one that, not only provides protection from arcs, but one that limits the time in which an arc is applied to a sample. Such a system would have less of a chance of startling users and would prevent destruction of valuable cells. The present invention provides a solution that addresses these issues.

SUMMARY OF THE INVENTION

The present invention provides both a system and method for reducing or quenching arcs during electroporation.

Generally, the system and method of the present invention provide for a current diverting circuit, which is operable to divert current away from a sample of biological cells involved in an electroporation session, so that the cells are not damaged by excess current should arc-over commence.

According to one aspect of the invention, the salient components of the system include: a charge control circuit; a high voltage capacitor, which accumulates charge provided by the charge control circuit; a microcontroller, which is capable of controlling the transfer of energy to a cuvette containing a suspension of biological cells; and a current diverter.

According to another aspect of the invention, the microcontroller monitors the voltage drop across the high voltage capacitor by employing a voltage divider at one of its inputs. When a first predetermined voltage is reached, the microcontroller takes action to cause the charging means to decouple from the high-voltage capacitor and trigger a first high-voltage switch, which functions to couple the high voltage capacitor to the cuvette containing the sample.

According to another aspect of the invention, the current diverter circuit includes a sense resistor, which is connected between the first high-voltage switch and ground. When the voltage drop across the sense resistor exceeds a second predetermined voltage, a current diverter switch is triggered, which functions to divert current away from the sample and then to ground.

In yet another aspect of the invention, a method is described which, when applied, reduces the amount of time during which a high voltage is applied to a cuvette containing a sample of cells when an arc-over event occurs or when the sample resistance is detected to be below a first predetermined value. The method comprises the steps of: (i) charging a high-voltage capacitor to a first predetermined voltage; (ii) triggering a high-voltage switch to couple substantially all of the first predetermined voltage of the capacitor to electrodes of the cuvette; (iii) monitoring the voltage applied across the cuvette; and (iv) triggering a current diverter switch when the monitored voltage is larger than a second predetermined voltage.

DESCRIPTION OF THE SPECIFIC EMBODIMENTS

Figure 2:
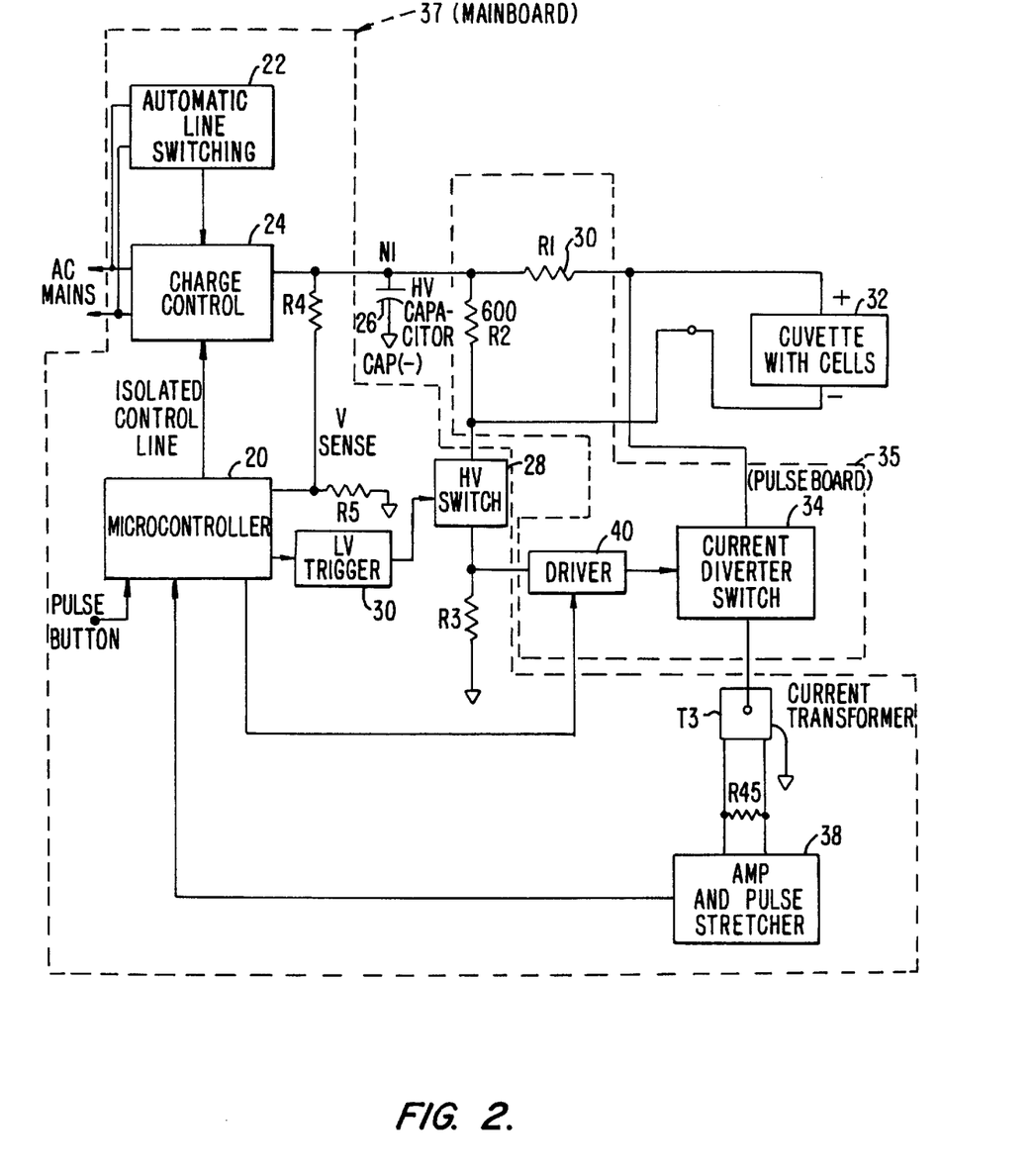
FIG. 2 is a block diagram of a preferred embodiment of the arc prevention/reduction components according to the system of the present invention.

The system of the present invention is shown generally in the block diagram of FIG. 2. In this exemplary embodiment, the system is comprised of a main board 37 and a pulse board 35. The main board 37 is comprised of the automatic line switching circuit 22, charge control circuitry 24, microcontroller 20, low voltage (LV) trigger 30, high-voltage (HV) switch 28, resistors R4 and R5, current transformer T3 and amplifier/pulse stretcher 38. The pulse board 35 is comprised of the driver 40, current diversion switch 34 and resistors R1 and R2. The remaining elements of FIG. 2, i.e., the AC Mains lines, cuvette 32 and HV capacitor 26 are located off-board.

As described in more detail below, the main board 37 operates to apply an exponentially decaying pulse, having an amplitude within a range of about 200 to 3000 volts, to the cuvette 32. The time constant of the exponential pulse is determined by the parallel combination of the sample resistance and R2 in conjunction with the capacitance of off-board HV capacitor 26 (typically 10 mfd, 3500 volts). As an example, using a standard *E. coli* sample, having a typical resistance of 3000 ohms, the time constant is approximately 5 msec.

Referring to FIG. 2, the AC Mains lines are coupled to an automatic line switching circuit 22 and a charge control circuit 24 on the main board. Automatic line switching allows the main board to accept different world voltages within the ranges of 100 to 120 volts and 220 to 240 volts and with an allowed +/−10% over/under tolerance.

Figure 3:
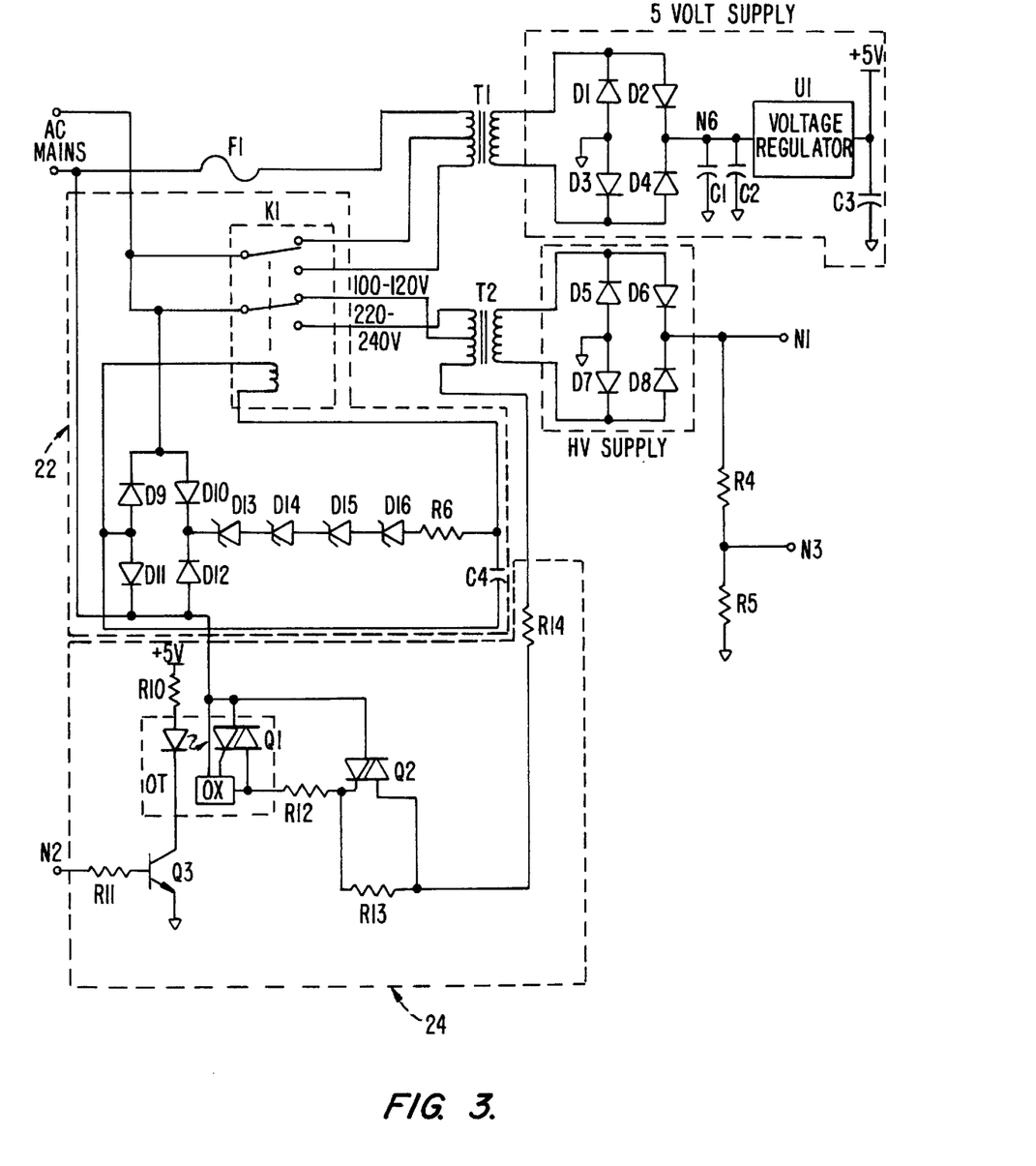
FIG. 3 is a schematic diagram of the charge control circuitry and automatic line switching circuitry according to the system of the present invention.

FIG. 3 is a more detailed schematic of the automatic line switching circuit 22 and charge control circuit 24. The automatic line switching circuit 22 operates as follows. First, if the AC Mains voltage is between 90 and 132 volts RMS, power is routed to the center taps of both transformers T1 and T2. If the AC Mains voltage is between 198 and 264 volts RMS, power is routed across the full windings of both transformers T1 and T2. However, transformer T2 is only powered when the triac Q1 is turned on. The secondary winding of transformer T2 powers a full-wave rectifier bridge comprised of diodes D5 through D8, which operate to charge the off-board HV capacitor 26 (see FIG. 2) at node N1.

The AC Mains voltage is also full-wave rectified by the diode bridge, comprising diodes D9 through D12, to produce a pulsating DC voltage, which is applied to a string of zener diodes D13 through D16. If the AC Mains voltage is from about 90 to 132 volts RMS, the zener diodes D13 through D16 do not conduct, and the voltage at the coil of double pole relay K1, which is produced through R6 and C4, is essentially zero. Hence, the center taps of transformers T1 and T2 are powered, and one secondary operates in an auto-transformer mode. If, on the other hand, the AC Mains voltage is from about 198 to 264 volts RMS, zener diodes D13 through D16 conduct sufficiently on peaks of the DC waveform (filtered through R6 and C4), such that coil of relay K1 has sufficient voltage to actuate the switches of the relay K1. If for some reason the automatic line switching fails, a main board fuse F1 will blow.

The secondary of transformer T1 drives another full-wave rectifier bridge comprised of diodes D1 through D4, which produces a voltage at capacitors C1 and C2. For typical line voltage ranges, this voltage is within the range of 8.0 to 13.5 volts. U1 is a five volt regulator, which produces a stable 5 volt supply in a 4.75–5.25 range. C1 operates as a main storage reservoir in the 5 volt section, whereas capacitors C2 and C3 prevent regulator U1 from oscillating.

The charge control circuitry 24 of FIG. 2 is also shown in more detail in FIG. 3. The microcontroller 20 (see FIG. 1) is configured to initiate, among other things, charging of the off-board HV capacitor 26. The microcontroller 20 performs this function by first signaling a monostable multivibrator U3 of FIG. 7. The monostable multivibrator U3 responds by providing a voltage pulse at node N2. A high voltage at node N2 turns transistor Q3 on. When transistor Q3 is on, current flows through the LED portion of the opto-triac OT. At zero crossing, the triac portion of the opto-triac OT turns on, which then turns on the main triac Q2 through resistors R12 and R13. The main triac Q2 then powers the primary winding of transformer T2. The secondary winding of the transformer T2 is then full-wave rectified by the diode bridge comprised of diodes D5 through D8 and the rectified voltage is used to charge the off-board HV capacitor 26 at node N1. The microcontroller 20 monitors the voltage across the HV capacitor 26 at node N3, by means of a precision voltage divider comprised of resistors R4 and R5. When the microcontroller detects a predetermined voltage being applied across the HV capacitor 26, it causes the charge control circuitry 24 to shut off.

Referring to FIG. 2, it is seen that one end of the HV switch 28 is coupled to the negative electrode of the cuvette 32. This negative electrode is essentially at ground potential. Once triggered, the HV switch 28 allows the high-voltage stored on the HV capacitor 26 to be applied to the cuvette 32. Current limiting resistor R1 is typically 30 ohms. It is employed as a current limiting resistor to protect against a direct short from occurring across the cuvette 32 and sample within. The resistance of the current limiting resistor R1 is small, relative to the sample resistance, which is, for example, in the range of 3000 ohms (E. Coli sample).

Resistor R2 is typically 600 ohms. So, it too is smaller than the typical sample resistance. Hence, when the HV switch 28 is triggered, nearly all the high voltage from the HV capacitor 26 will discharge to ground through resistors R2 and R3. (R3 is a current sense resistor (typically 0.1 ohms) and has no significant effect on the pulse applied to the sample.)

Figure 4:
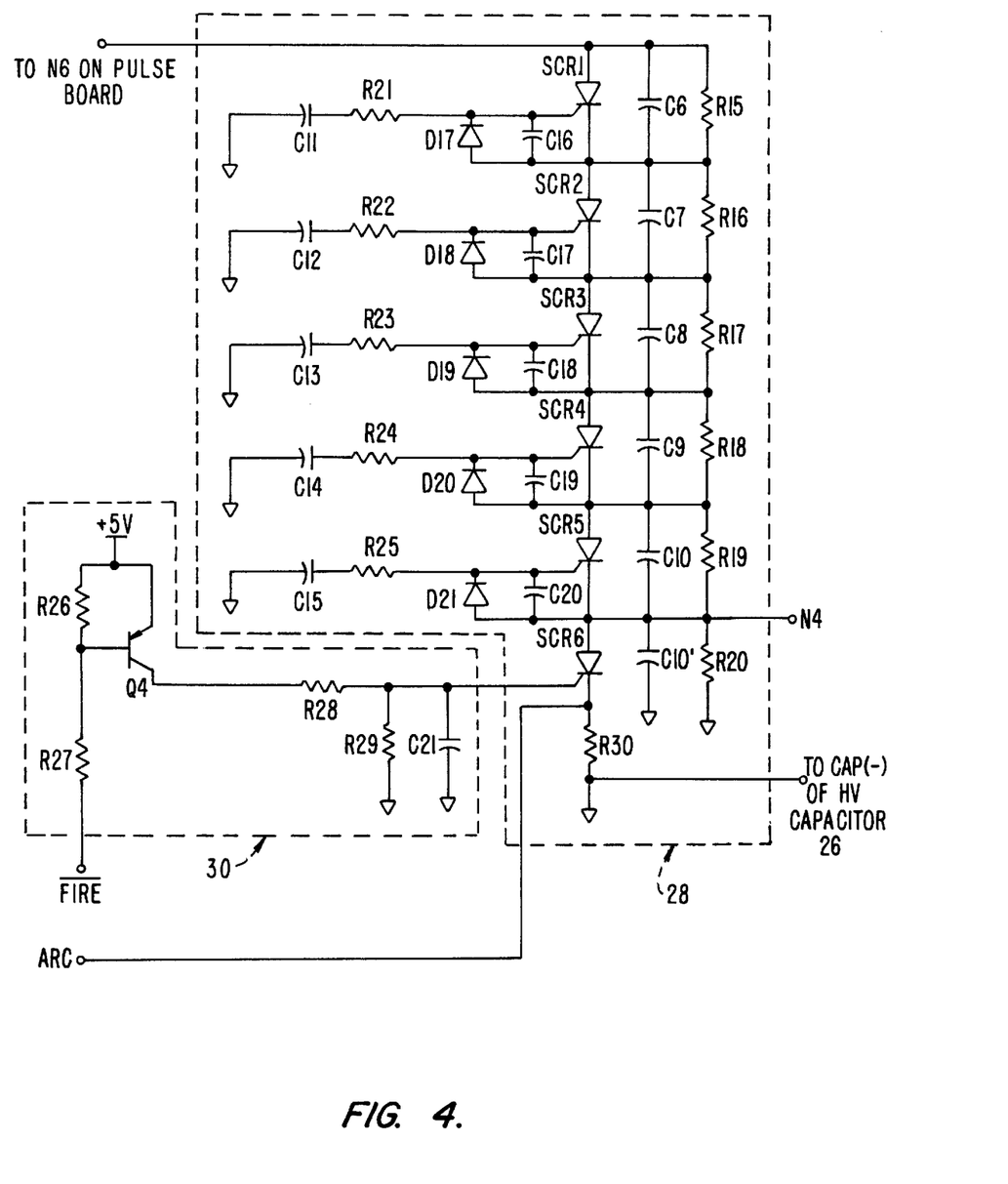
FIG. 4 is a schematic diagram of the LV trigger circuitry and HV switch circuitry according to the system of the present invention.

FIG. 4 illustrates a detailed schematic of the HV switch 28 and a detailed representation of the low voltage (LV) trigger circuit 30, which are identified by the dashed boxes in FIG. 4. The operational characteristics of the HV switch 28 are disclosed in U.S. Pat. No. 4,750,100, which is hereby incorporated in this disclosure by reference.

Referring to FIG. 4, the HV switch 28 is formed from a series of silicon control rectifiers (SCRs) SCR1 through SCR6. Each of the SCRs SCR1 through SCR5 are shunted with shunt resistors R15 through R20 and shunt capacitors C6 through C10. The shunt resistors R15 through R20 operate to equalize the voltage across each of the SCRs SCR1 through SCR5. This function of equalizing the voltage across each SCR is important, particularly when the SCRs are in their blocking (non-conducting) states. Because there may be variations in the blocking characteristics among the SCRs, unequal steady-state sharing among the SCRs could arise. Without the shunt resistors R15 through R20 those SCRs SCR1 through SCR5 that have inherently low current blocking capabilities could be damaged, since an excessive voltage could appear across those SCRs.

The shunt capacitors C6 through C10' perform a similar function as the shunt resistors R15 through R20, except they operate when the SCRs SCR1 through SCR5 are turning on and off, i.e. when they are not in a steady-state of non-conductance. The shunt capacitors C6 through C10' act as open circuits when the SCRs are in their non-conducting states. When the delay time of one SCR is longer relative to another, a higher voltage drop will occur across the slower SCR. Accordingly, the shunt capacitors C6 through C10' perform voltage equalization across the SCRs SCR1 through SCR5.

In addition to the shunt resistors R15 through R20 and the shunt capacitors C6 through C10', an alternative embodiment could include a series of shunt metal oxide varistors (MOVs). This is disclosed in U.S. Pat. No. 4,750,100 (incorporated by reference above).

Diodes D17 through D21, which are coupled to the gates of SCRs SCR1 through SCR5, respectively, protect the gates of the SCRs SCR1 through SCR5 from transients and also ensure that the SCRs SCR1 through SCR5 never become reverse-biased. Capacitors C16 through C20 function to prevent the SCRs SCR1 through SCR5 from spuriously turning on.

Also connected to the gate of each SCR is a series combination of resistors R21 through R25 and capacitors C11 through C15, which are coupled to the gates of SCRs SCR1 through SCR5, respectively. Resistors R21 through R25 and capacitors C11 through C15 function to store sufficient charge in the capacitors C11 through C15 so that when SCR6 is turned on, it causes SCRs SCR5 through SCR1 to, in turn, turn on (in that order). The voltage at each capacitor C11 through C15 is divided by resistors R15 through R20 and connected by diodes D17 through D21. Once the last SCR (i.e. SCR1) has turned on, the HV switch 28 has effectively placed R2 (see FIG. 1) in parallel with the cuvette 32 (through current limiting resistor R1. If desired, the voltage drop across R2 can be increased by providing a greater number of SCR cells.

SCR6 is initially turned on by the LV trigger circuit 30, which is activated by the microcontroller 20 by bringing the $\overline{\text{FIRE}}$ signal low. When the microcontroller 20 drops $\overline{\text{FIRE}}$ low, transistor Q4 turns on an d the voltage at the gate of SCR6 is raised to a voltage of over 2 volts based on that portion of Q4's collector voltage that is dropped across the node connecting resistors R28 and R29. Capacitor C21 reduces the effect of transients at the gate of SCR6.

Once the SCRs SCR1 through SCR6 are turned on, they cannot turn off until the current flowing through them drops below the rated holding current (typically around 60 mA). Normal pulses applied to the cuvette 32 are pulses that decay exponentially over time as the HV capacitor 26 discharges through resistors R2 and R3. If, however, an arc-over condition commences or for some reason the sample resistance is too low, there must be some way to decouple the HV capacitor 26 from the cuvette 32 so that the sample is not damaged.

In the currently described embodiment, this is accomplished by monitoring the current that flows through the HV switch 28. Resistor R30 in FIG. 4 produces a pulse that is proportional to the current flowing in the HV switch 28. This pulse is applied to the circuitry on the pulse board 35 via connecting line labeled "ARC". When the current in HV switch 28 exceeds approximately 12 A, the current diverter switch 34 on the pulse board 35 is switched on by the firing of driver circuit 40.

Figure 5:
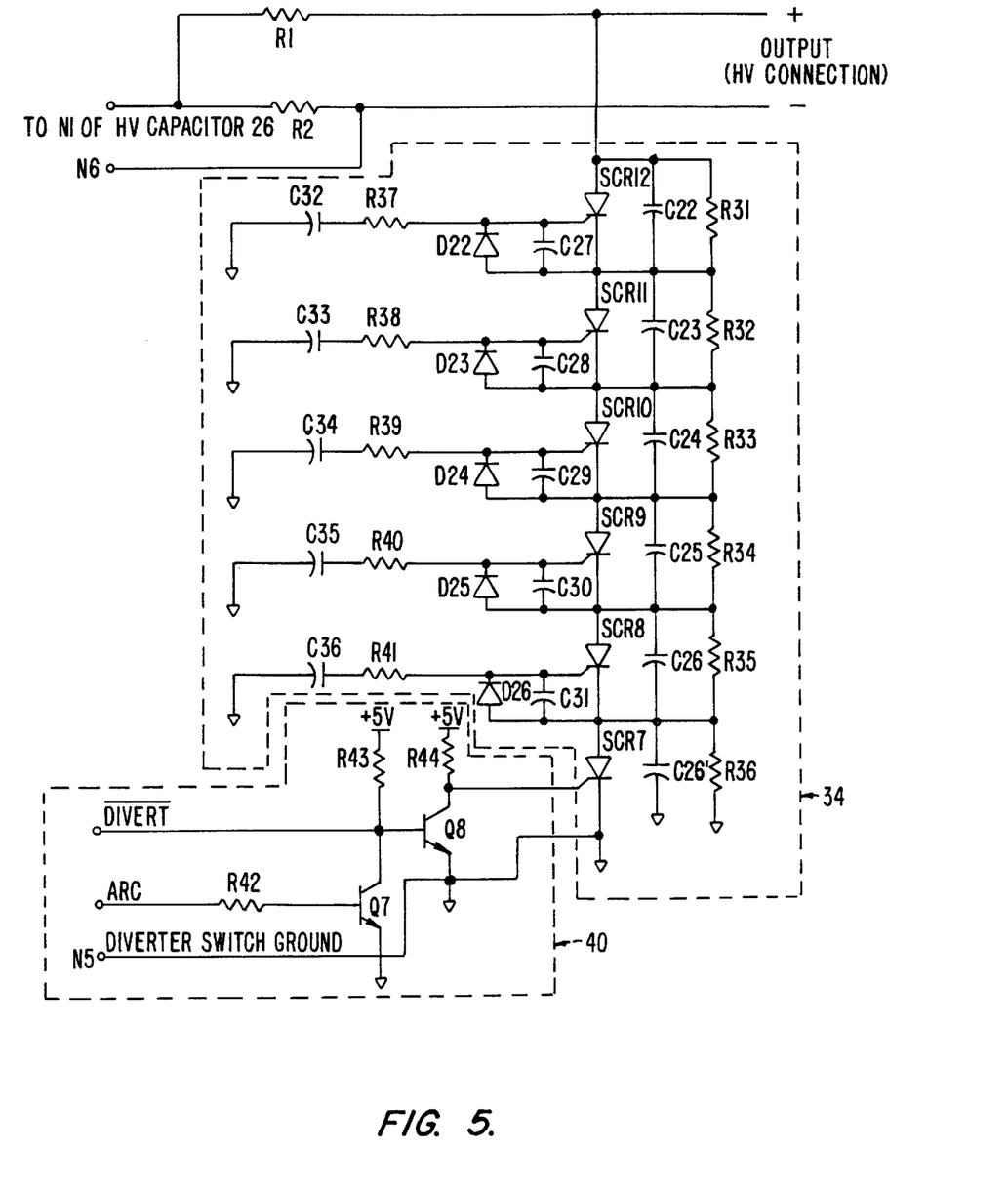
FIG. 5 is a schematic diagram of the driver circuitry and current diverter switch circuitry according to the system of the present invention.

The driver circuit 40 and current diverter switch 34 are shown in detail in FIG. 5. When an arc or low resistance event is detected the ARC line is asserted high and applied to the base of transistor Q7 via resistor 42. This causes transistor Q8 to turn off and the collector of Q8 to be pulled high so that SCR7 is triggered. The remaining SCRs, SCR8 through SCR12 are then rapidly turned on in succession in a manner described for the HV switch 28 in FIG. 4. In other words, referring to FIG. 4, the current diverter switch 34 is formed from a series of SCRs SCR7 through SCR12. Each of the SCRs SCR8 through SCR12 is shunted with shunt resistors R31 through R35 and shunt capacitors C22 through C26'. The shunt resistors R31 through R36 operate to equalize the voltage across each of the SCRs SCR8 through SCR12. This function of equalizing the voltage across each SCR is important, particularly when the SCRs are in their blocking (non-conducting) states. Because there may be variations in the blocking characteristics among the SCRs, unequal steady-state sharing among the SCRs could arise. Without the shunt resistors R31 through R36 those SCRs SCR8 through SCR12 that have inherently low current blocking capabilities could be damaged, since an excessive voltage could appear across those SCRs.

The shunt capacitors C22 through C26' perform a similar function as the shunt resistors R31 through R36, except they operate when the SCRs SCR8 through SCR12 are turning on and off, i.e. when they are not in a steady-state of non-conductance. The shunt capacitors C22 through C26' act as open circuits when the SCRs are in their non-conducting states. When the delay time of one SCR is longer relative to another, a higher voltage drop will occur across the slower SCR. Hence, the shunt capacitors C22 through C26' perform voltage equalization across the SCRs SCR8 through SCR12. An alternative embodiment would include a series of metal oxide varistors (MOVs).

Diodes D22 through D26, which are coupled to the gates of SCRs SCR8 through SCR12, protect the gates of the SCRs SCR8 through SCR12 from transients and also ensure that the SCRs SCR8 through SCR12 never become reverse-biased. Capacitors C27 through C31 function to prevent the SCRs SCR8 through SCR12 from spuriously turning on.

Also connected to the gate of each SCR is a series combination of resistors R37 through R41 and capacitors C32 through C36, which are coupled to the gates of SCRs SCR8 through SCR12. Resistors R37 through R41 and capacitors C32 through C36 function to store sufficient charge in the capacitors C32 through C36 so that when SCR7 is turned on, it causes SCRs SCR8 through SCR12 to, in turn, turn on (in that order). The voltage at each capacitor C32 through C36 is divided by resistors R31 through R36 and connected by diodes D22 through D26.

Once the current diverter switch 34 is turned, current flow is diverted from the resistor R2-HV switch 28—resistor R3 path and through the current diverter switch 34.

In the currently described embodiment, the time that elapses between detection of an arc-over event (or low resistance condition) and the triggering of the current diverter switch 34, is very short. Consequently, only a very narrow pulse or essentially no pulse at all is applied to the sample during this span of time. A pulse of such short duration (typically about 5 microseconds in the currently described embodiment) prevents the sample cells from being damaged.

Detection of an arc-over event (or low resistance condition) is performed exclusive of microcontroller 20 control. To protect the sample once an arc-over event is detected, the time that elapses between detection of the arc-over event and the time that appropriate remedial action must be taken is shorter than the time in which the microcontroller 20 of the currently described embodiment can detect and respond. However, it is conceivable that if a high-speed microcontroller were available, such detection could take place.

Figure 6:
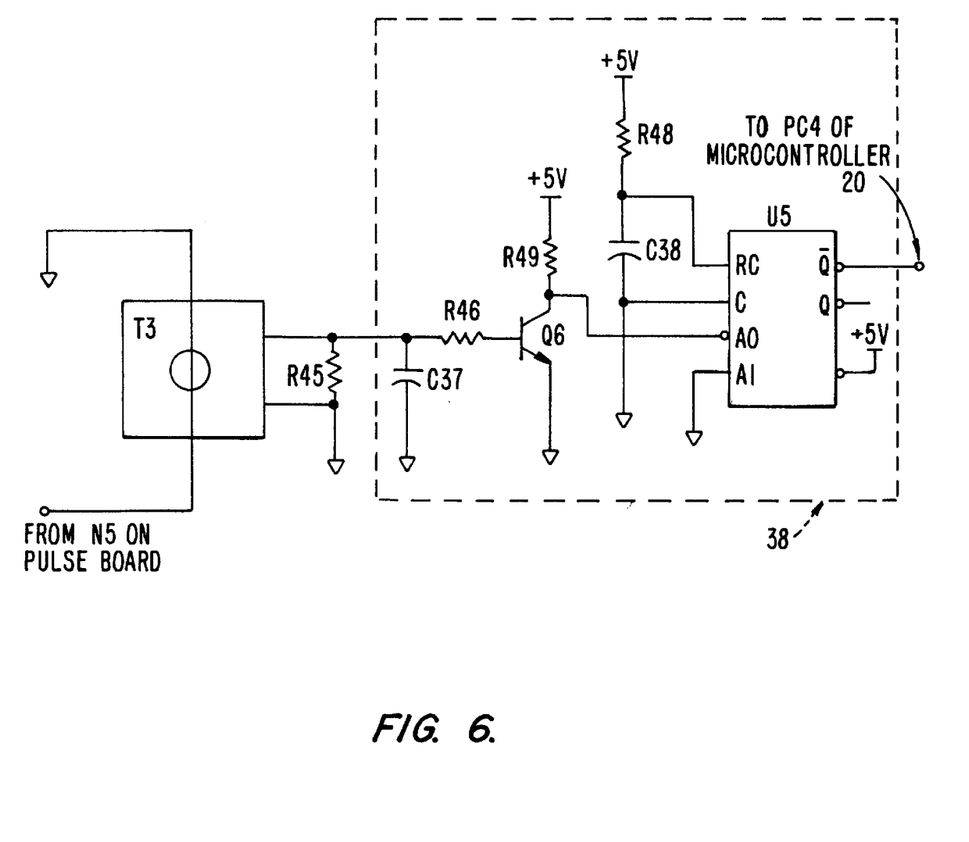
FIG. 6 is a schematic diagram of the current transformer and amplifier/pulse stretcher circuitry according to the system of the present invention.

Nevertheless, the system of the current invention provides a technique, which allows the microcontroller to receive notification that an arc-over event (or low resistance condition) has occurred. The circuit that accomplishes this task is shown in FIG. 6. Referring to FIGS. 5 and 6, when the current diverter switch 34 on the pulse board 36 fires, its ground current is transferred to the main board 37 and through the current transformer T3 (see node 5 in FIGS. 5 and 6). The output of current transformer T3 is coupled to the base of transistor Q6, via resistors R45 and R46 and capacitor C37, which causes transistor Q6 to turn on. When transistor Q6 turns on, the input A0 of one-shot U5 operates to stretch the narrow pulse of a detected arc or low-resistance event. The degree to which the pulse is stretched is controlled by selecting the appropriate combinations of the resistance of resistor 48 and capacitance of capacitor C38. Stretching of the pulse provides the relatively slow microcontroller 20 the ability to receive notification that an arc-over (or low resistance condition) has occurred and detected.

Figure 7:
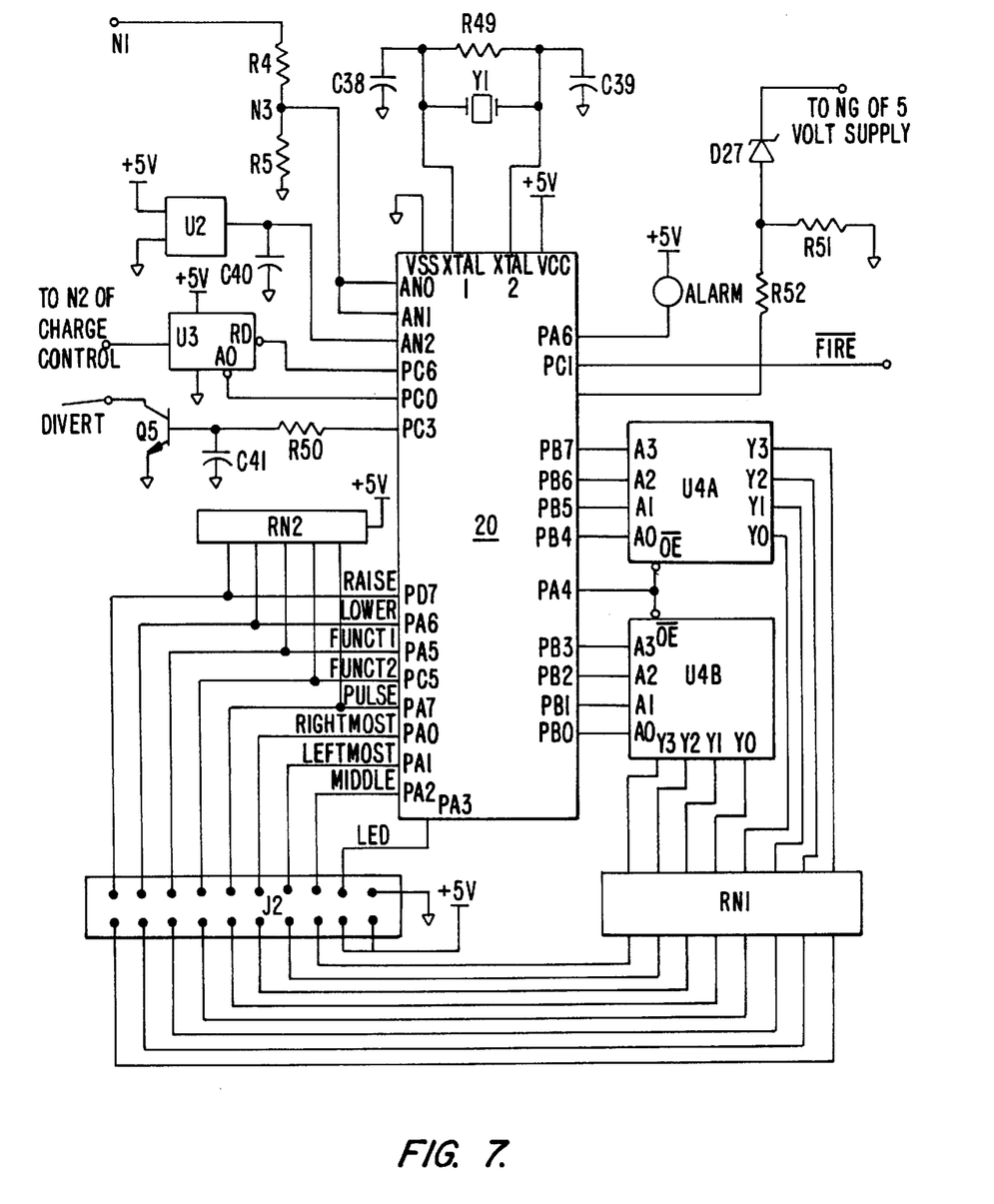
FIG. 7 is a schematic diagram of the microcontroller and associated circuitry according to the system of the present invention.

Referring now to FIG. 7, there is shown the microcontroller 20 of FIG. 1 and its various connections, according to a preferred embodiment of the system of the present invention. Preferably, the microcontroller 20 is a Motorola MC68HC705SRC3P CMOS processor. It is powered with a 5 volt supply and operates at a clock frequency of 2 MHz. The clock is divided by two, such that the data processing (or cycle) time is 1 microsecond. The clock is generated with the microcontroller 20 by crystal Y1, capacitors C38 and C39 and resistor R49.

With the exception of detecting an arc-over event (or low sample and/or cuvette 32 resistance condition), the microcontroller 20 controls most of the operations of the system. It interfaces to a display module (not shown in FIG. 8), reads switches and multiplexes the displays. Communication to the display module is by means of connector J2. Displays are divided into four banks (Rightmost, Leftmost, Middle and LED), with each bank driven by bank drivers located external to the main board 37. Each bank is powered for at least 2 msec, resulting in a rate that is fast enough for the eye to see a continuous display. The banks are controlled by PA0 through PA3 of the microcontroller 20, and only one bank is powered at a time. Segments of the displays are selected by a bit pattern on Port B (PB0 through PB7) and driven by buffers U4A and U4B (preferably device no. 74LS244A).

Switch lines enter the main board 37 also by means of J2, and the lines are pulled up to 5 volts by resistors in resistor bank RN2. Actuation of a key switch pullsdown the lines, which connect to PD7, PD6, PA5, PC5 and PA7 of the microcontroller 20. These switches allow the user to change the characteristics of the pulse applied to the cuvette 32, e.g. pulse peak voltage, time between successive pulses, pulse width, etc. A pulse button is also provided so that a user can manually apply a pulse to the sample.

The microcontroller 20 may also sound an alarm by "twitching" PA6 to notify the user of the detection of an arc-over event or (low resistance condition).

R4 and R5 form a precision voltage divider to provide approximately 0 to 4.75 volts to two parallel A/D inputs, AN0 and AN1 to the microcontroller 20 when the HV capacitor 26 is 0 to 3000 volts. U2 is a precision 2.500 volt reference (10 mV accuracy, low drift) that is applied to AN2. The output voltage of voltage reference U2 is converted to a digital number, which is used to scale the numbers derived on the other A/D channels. Since the voltage at AN0 and AN1 on the microprocessor is an accurate representation of the pulse amplitude, these numbers can be scaled by the number determined at AN2 to compensate for the variation produced by the 5V power supply. The result is a stable system in no need of adjustment. Additionally, if the numbers at AN2 are not within a certain range, the microprocessor can revert to an error mode, indicating that either the A/D channel or U2 is faulty.

The microcontroller 20 can also be configured to turn on the current diverter switch 34 by asserting PC3 (see FIG. 7) and turning on transistor Q5. This allows the microcontroller 20 to produce a time-truncated exponential waveform as directed by the user or a program. If the microcontroller 20 diverts current to produce a time-truncated exponential, the current transformer T3 will sense the current, and a signal will be sent to the microcontroller 20. The system is programmed, however, to ignore the information, since such information is expected when producing a truncated exponential.

U3, a retriggerable monostable multivibrator, is configured to function as a safety mechanism, whereby the charge control circuitry 24 can initiate a charging only if two signals from the microcontroller 20, PC0 and PC6, are present and of the correct logic level. Charging commences only if PC0 is asserted low and PC6 is "twitched" low. This causes U3 to provide an essentially continuous pulse unless the microcontroller 20 program flow is disrupted, in which case the "twitch" from PC6 will not occur and further charging will be prevented.

Another safety feature relates to the prevention of having 220V from the AC mains supplied to C1 should the switch of relay K1 become stuck in the 120V position. If this fault should occur, the voltage across C2 (node N6) will rise, causing zener diode D27 to conduct and prevent the diode in opto-triac OT from conducting (reversed biased). Charging would then be prevented. Zener diode D27 preferably terminates in a resistor R51 to ground and the junction of this resistor R51 and zener diode D27 is supplied through another resistor R52 to input PC7 of the microcontroller 20. When a fault occurs, D27 conducts and informs the microcontroller 20. The microcontroller 20 responds by indicating to the user that an error has occurred and prevents the charge control circuitry 24 from continuing to charge.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An electroporator system for directing a high-voltage current through a suspension of biological cells contained in a cuvette, the system comprising a current diverting circuit that diverts current away from the cells whenever an arc event or low sample resistance is detected.

2. An apparatus for protecting against arcing across a cuvette containing a sample of biological cells in an electroporator system, comprising:
   (a) a HV capacitor;
   (b) a charge control circuit, which provides a voltage to a HV capacitor;
   (c) a microcontroller coupled to the charge control and configured to:
      (1) cause the charge control to decouple from the HV capacitor, and
      (2) trigger a HV switch to couple the HV capacitor to the cuvette,
      when the voltage drop across the HV capacitor equals a predetermined voltage; and
   (d) a current diverter circuit, which diverts current flow away from the cuvette when an arc event or low sample resistance is detected.

3. The apparatus of claim 2, further comprising a voltage divider circuit, coupled to the input of the microcontroller, and which, in conjunction with the microcontroller, is operable to monitor the voltage drop across the HV capacitor.

4. The apparatus of claim 2, wherein the microcontroller is configured to control the current diverter circuit in a manner that permits a plurality of different types of waveforms to be applied to the cuvette.

5. The apparatus of claim 2, wherein the current diverter circuit is triggered by a voltage dropped across a sense resistor, the sense resistor coupled between the HV switch and ground.

6. The apparatus of claim 2 further comprising an automatic line switching circuit coupled to the AC mains and charge control, the automatic line switching circuit capable of accepting different world voltages within the ranges of approximately 100 to 120 volts and 220 to 240 volts.

7. The apparatus of claim 2, further comprising a current-limiting resistor, coupled between the HV capacitor and the cuvette, and which is operable to further decrease the likelihood of arcs occurring across the cuvette.

8. The apparatus of claim 5, further comprising a current transformer that triggers an amplifier and pulse stretcher to provide a pulse to the microcontroller, whenever the current diverter circuit is triggered, so as to notify the microcontroller that an arc event or detection of a low sample resistance condition has occurred.

9. The apparatus of claim 2 wherein the microcontroller is electrically isolated from the charge control.

10. The apparatus of claim 2 wherein the microcontroller is capable of triggering the current diverter circuit to produce a time-truncated exponential pulse that is applied to the cuvette.

11. A method of reducing the duration of time of which a high voltage is applied to a cuvette containing sample of cells, when an arc-over event occurs or when the sample resistance is detected to be below a predetermined value, the method comprising the steps of:
   (a) charging a HV capacitor to a first predetermined voltage;
   (b) triggering a HV switch to couple substantially all of the first predetermined voltage of the capacitor to electrodes of the cuvette;
   (c) monitoring the voltage applied across the cuvette; and
   (d) triggering a current diverter switch when the monitored voltage is larger than a second predetermined voltage.

12. The method of claim 11 wherein the steps of triggering the HV switch and monitoring the voltage applied across the cuvette are performed under the control of a microcontroller.

13. The method of claim 1 wherein a time-truncated exponential pulse can be applied to the sample.

14. A method of manufacturing an electroporator system containing a sample of biological cells capable of preventing or reducing an arcing event across a cuvette, comprising the steps of:
   (a) providing a HV capacitor;
   (b) providing a charge control, capable of establishing a voltage drop across the HV capacitor;
   (c) providing a microcontroller that is capable of:
      (1) causing the charge control to decouple from the HV capacitor, and
      (2) triggering a HV switch to couple the HV capacitor to the cuvette,
      when the voltage drop across the HV capacitor equals a predetermined voltage; and
   (d) providing a current diverter switch, capable of diverting current flow away from the cuvette when an arc event commences.

15. The method of claim 14, further comprising the step of providing a voltage divider circuit, coupled to the input of the microcontroller, and which, in conjunction with the microcontroller, is capable of monitoring the voltage drop across the HV capacitor.

16. The method of claim 14, wherein the microcontroller is capable of controlling the current diverter switch in a manner that permits a plurality of different types of waveforms to be applied to the cuvette.

17. The method of claim 14, wherein the step of providing the current diverter switch includes providing a sense resistor, coupled between the HV switch and ground, and which is capable of detecting a second voltage and triggering the current diverter switch when the sense resistor detects commencement of an arc event.

18. The method of claim 14, further comprising the step of providing a current-limiting resistor, coupled between the high-voltage capacitor and the cuvette, and which is capable of decreasing the likelihood of arcs occurring across the cuvette.

19. The method of claim 17, further comprising the steps of:
   (a) providing a current transformer, and
   (b) providing a pulse stretcher,
wherein the current transformer is capable of triggering the pulse stretcher, when current is diverted from the cuvette, and the pulse stretcher is capable of providing a pulse to the microcontroller so as to inform the microcontroller that an arc event has commenced.

* * * * *